US00PP33740P2

(12) United States Plant Patent
Arts

(10) Patent No.: US PP33,740 P2
(45) Date of Patent: Dec. 14, 2021

(54) ***HYDRANGEA* PLANT NAMED 'H220914'**

(50) Latin Name: *Hydrangea macrophylla*
Varietal Denomination: H220914

(71) Applicant: HYDRANGEA BREEDERS ASSOCIATION B.V., De Kwakel (NL)

(72) Inventor: Niels Arts, Aalsmeer (NL)

(73) Assignee: Hydrangea Breeders Association B.V., De Kwakel (NL)

( * ) Notice: Subject to any disclaimer, the term of this patent is extended or adjusted under 35 U.S.C. 154(b) by 0 days.

(21) Appl. No.: 17/240,936

(22) Filed: Apr. 26, 2021

(51) Int. Cl.
*A01H 5/00* (2018.01)
*A01H 6/48* (2018.01)

(52) U.S. Cl.
USPC ..... Plt./250

(58) Field of Classification Search
USPC ..... Plt./226, 250
See application file for complete search history.

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct cultivar of *Hydrangea* plant named 'H220914', characterized by its relatively compact, upright and uniformly mounded plant habit; vigorous growth habit and rapid growth rate; freely branching habit with strong, thick and sturdy stems; freely and uniformly flowering habit; large mophead-type inflorescences with numerous purplish pink-colored sterile flowers; and good postproduction longevity.

3 Drawing Sheets

Figure 1:
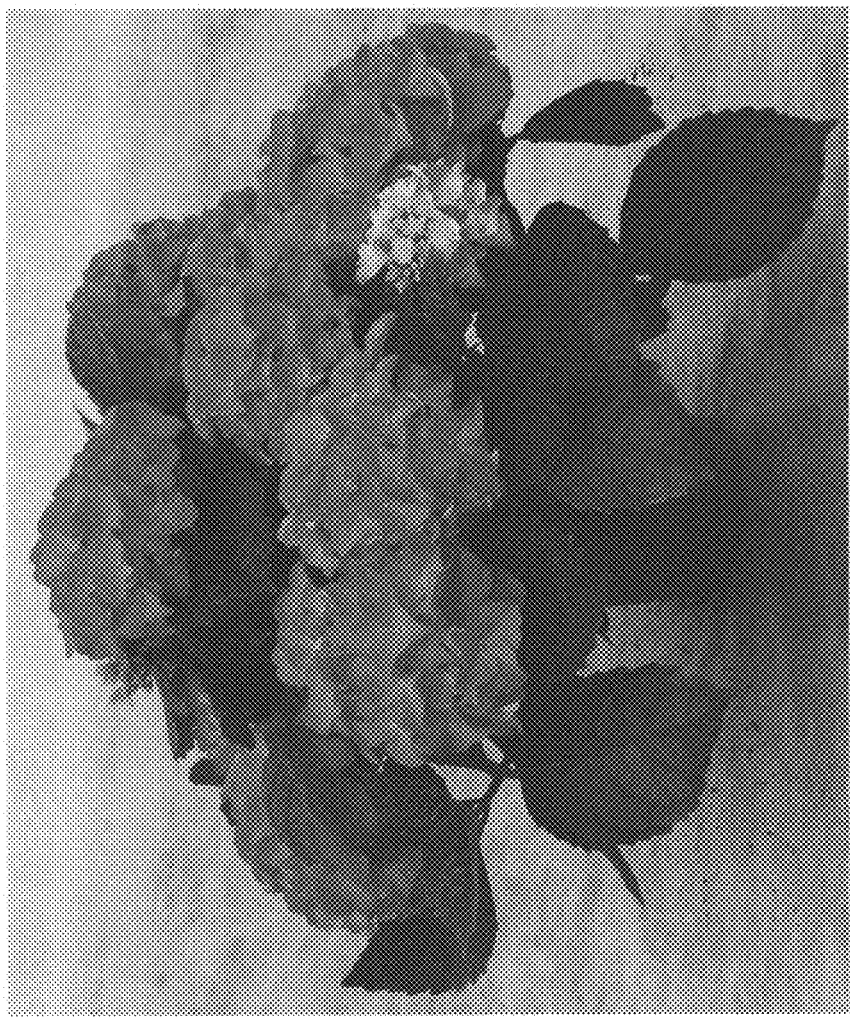

Botanical designation: *Hydrangea macrophylla.*
Cultivar denomination: 'H220914'.

CROSS-REFERENCED TO CLOSELY-RELATED APPLICATIONS

Title: *Hydrangea* Plant Named 'H220913'
Inventor: Niels Arts
Applicant: *Hydrangea* Breeders Association B.V.
Filed: Concurrently with the instant application U.S. patent application Ser. No. 17/240,929

STATEMENT REGARDING PRIOR DISCLOSURES BY INVENTOR & APPLICANT/ASSIGNEE

An European Community Plant Breeder's Rights application for the instant plant was filed by the Applicant/Assignee, *Hydrangea* Breeders Association B.V. of De Kwakel, The Netherlands on Jan. 4, 2021, application number 2021/0010. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'H220914'.

The new *Hydrangea* plant is a product of a planned breeding program conducted by the Inventor in Dresden and Lengerich, Germany. The objective of the breeding program was to create new strong and freely-branching *Hydrangea* plants with strong sturdy stems, uniform flowering habit, large inflorescences with numerous showy sterile flowers, attractive sterile flower color and good postproduction longevity.

The new *Hydrangea* plant originated from an open-pollination in April, 2014 in Dresden, Germany, of *Hydrangea macrophylla* 'Tabletensia', not patented, as the female, or seed, parent with an unknown selection of *Hydrangea macrophylla* as the male, or pollen, parent. The new *Hydrangea* plant was discovered and selected by the Inventor as a single flowering plant from within the progeny of the stated open-pollination in a controlled greenhouse environment in Lengerich, Germany in April, 2016.

Asexual reproduction of the new *Hydrangea* plant by vegetative tip cuttings in a controlled environment in Lengerich, Germany since July, 2016 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'H220914'. These characteristics in combination distinguish 'H220914' as a new and distinct *Hydrangea* plant:

1. Relatively compact, upright and uniformly mounded plant habit.
2. Vigorous growth habit and rapid growth rate.
3. Freely branching habit with strong, thick and sturdy stems.
4. Freely and uniformly flowering habit.
5 Large mophead-type inflorescences with numerous purplish pink-colored sterile flowers.
6. Good postproduction longevity.

Plants of the new *Hydrangea* can be compared to plants of the female parent, 'Tabletensia'. Plants of the new *Hydrangea* differ primarily from plants of 'Tabletensia' in the sterile flower color as sterile flowers of plants of the new *Hydrangea* are darker purplish pink in color than sterile flowers of plants of 'Tabletensia'.

Plants of the new *Hydrangea* can be compared to plants of *Hydrangea macrophylla* 'H220913', disclosed in a U.S. Plant Patent application filed concurrently. Plants of the new *Hydrangea* differ primarily from plants of 'H220913' in sterile flower color as plants of the new *Hydrangea* have purplish pink-colored sterile flowers whereas plants of 'H220913' have purplish red-colored sterile flowers.

Plants of the new *Hydrangea* can be compared to plants of the *Hydrangea macrophylla* '200749077', disclosed in U.S. Plant Pat. No. 16,441. In side-by-side comparisons, plants of the new *Hydrangea* differ primarily from plants of '200749077' in the following characteristics:

1. Plants of the new *Hydrangea* more compact than plants of '200749077'.
2. Plants of the new *Hydrangea* are more freely branching than plants of '200749077'.
3. Plants of the new *Hydrangea* have slightly smaller leaves than plants of '200749077'.
4. Plants of the new *Hydrangea* have more sterile flowers per inflorescence than plants of '200749077'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1) is a side perspective view of a typical flowering plant of 'H220914'.

Figure 2:
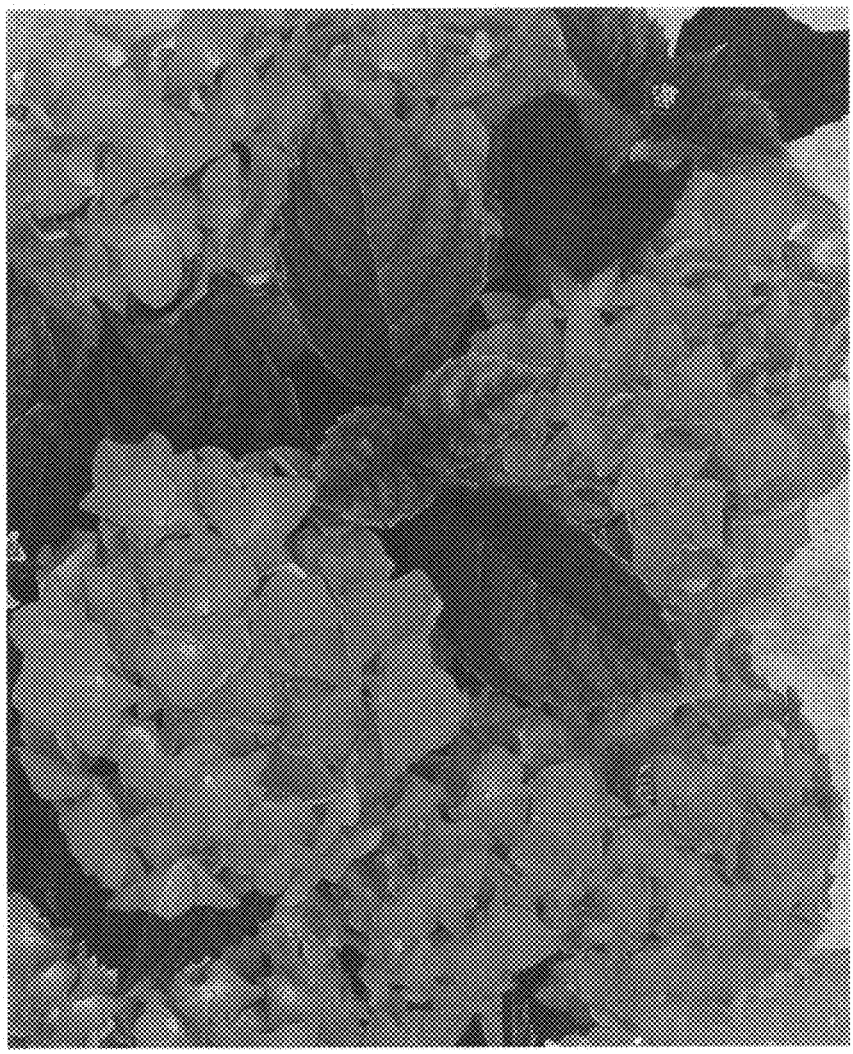

The photograph on the second sheet (FIG. 2) is a close-up view of typical inflorescences of 'H220914'.

Figure 3:
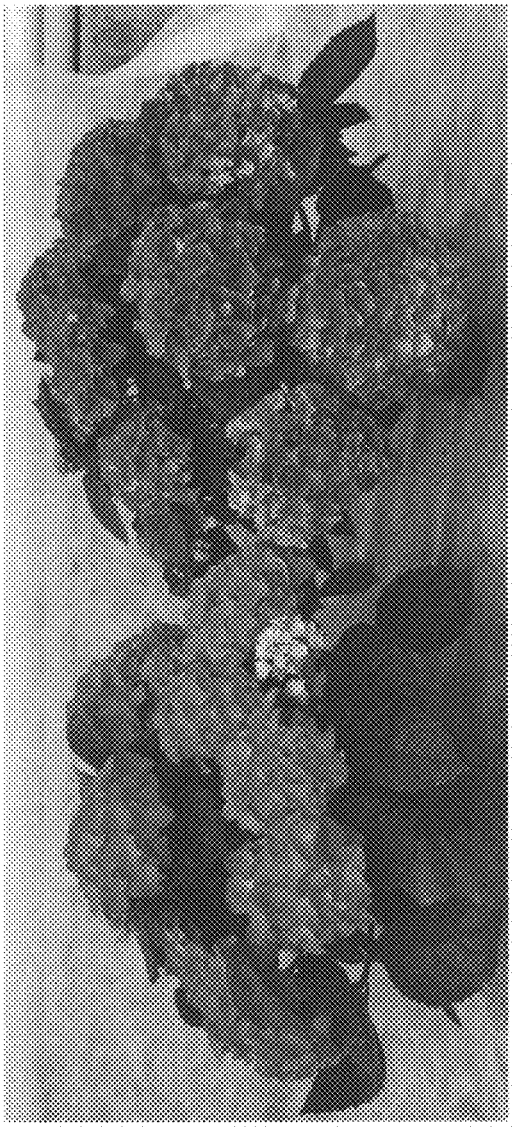

The photograph on the third sheet (FIG. 3) is a side perspective view on the left of a typical flowering plant of 'H220914' that has not been "blued", that is, treated with aluminum sulfate, and a side perspective view on the right of a typical flowering plant of 'H220914' that has been "blued".

DETAILED BOTANICAL DESCRIPTION

Plants used in the aforementioned photographs and in the following description were grown during the spring and early summer in 13-cm containers in a glass-covered greenhouse in Lengerich, Germany and under cultural practices typical of commercial *Hydrangea* production. During the production of the plants, day and night temperatures averaged 17° C. Plants of the new *Hydrangea* were one year old when the photographs and description were taken. Plants of the new *Hydrangea* can be successfully treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea macrophylla* 'H220914'.

Parentage:

*Female, or seed, parent.*—*Hydrangea macrophylla* 'Tabletensia', not patented.

*Male, or pollen, parent.*—Unknown selection of *Hydrangea macrophylla*, not patented.

Propagation:

*Type cutting.*—By vegetative tip cuttings.

*Time to initiate roots, summer.*—About two weeks at temperatures about 23° C.

*Time to initiate roots, winter.*—About 18 days at temperatures about 20° C.

*Time to produce a rooted young plant, summer.*—About four weeks at temperatures about 23° C.

*Time to produce a rooted young plant, winter.*—About five weeks at temperatures about 20° C.

*Root description.*—Thick; typically whitish brown in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Relatively compact, upright and uniformly mounded plant habit; strong and sturdy stems; rapid growth rate and vigorous growth habit.

*Plant height.*—About 22 cm to 25 cm.

*Plant diameter or area of spread.*—About 40 cm to 45 cm.

Lateral branch description:

*Branching habit.*—Freely branching habit; when pinched, about twelve lateral branches develop per plant.

*Length.*—About 18 cm to 20 cm.

*Diameter.*—About 5 mm.

*Internode length.*—About 3 cm to 5 cm.

*Texture.*—Smooth, glabrous; fully developed, woody.

*Aspect.*—Upright to slightly outward.

*Strength.*—Strong, sturdy.

*Color.*—When developing: Close to 146C; at internodes, close to 187A; lenticels, close to 187A. Developed: Close to 146C; at the internodes, close to 187A; when woody, close to 177D; lenticels, close to 187A.

Leaf description:

*Arrangement.*—Opposite, simple.

*Length.*—About 10 cm to 12 cm.

*Width.*—About 6 cm to 8 cm.

*Shape.*—Elliptic.

*Apex.*—Acute.

*Base.*—Obtuse.

*Margin.*—Dentate.

*Texture, upper surface.*—Smooth to rippled, glabrous.

*Texture, lower surface.*—Smooth, glabrous.

*Venation pattern.*—Pinnate.

*Color.*—Developing and fully expanded leaves, upper surface: Close to NN137B; venation, close to 146C.

Developing and fully expanded leaves, lower surface: Close to 138B; venation, close to 146D.

*Petioles*.—Length: About 2.5 cm. Diameter: About 4 mm. Texture, upper and lower surfaces: Smooth, glabrous. Color, upper surface: Close to 145B. Color, lower surface: Close to 145C.

Flower description:

*Flower type and habit*.—Showy sterile flowers and small inconspicuous fertile flowers arranged on mophead-type terminal panicles; panicles globular in shape; rounded fertile and sterile flowers face upright to outwardly depending on their position in the inflorescence.

*Fragrance*.—None detected.

*Natural flowering season*.—Plants flower naturally in the early summer and is continuous throughout the summer in Northern Europe.

*Flower longevity*.—Fertile and sterile flowers last about three months on the plant, fertile and sterile flowers persistent.

*Quantity of flowers*.—Freely flowering habit; about 30 fertile flowers per panicle and about 60 to 80 sterile flowers per panicle.

*Panicle height*.—About 8 cm.

*Panicle diameter*.—About 12 cm.

*Fertile flower buds*.—Length: About 4 mm. Diameter: About 4 mm. Shape: Rounded. Color: Close to 145C.

*Sterile flower buds*.—Length: About 5 mm. Diameter: About 3 mm. Shape: Rounded. Color: Close to 145C.

*Fertile flower diameter*.—About 4 mm.

*Fertile flower depth* (*height*).—About 2 mm.

*Sterile flower diameter*.—About 4 cm.

*Sterile flower depth* (*height*).—About 1 cm.

*Petals, fertile flowers*.—Quantity and arrangement: Four in a single whorl. Length: About 4 mm. Width: About 2 mm. Shape: Ovate. Apex: Acute. Base: Obtuse. Margin: Entire. Texture, upper and lower surfaces: Smooth, glabrous. Color: When opening, upper and lower surfaces: Close to 145C. Fully opened, upper and lower surfaces: Close to N57D; color does not change with development.

*Petals, sterile flowers*.—Quantity and arrangement: Four in a single whorl. Length: About 4 mm. Width: About 2 mm. Shape: Ovate. Apex: Acute. Base: Attenuate. Margin: Entire. Texture, upper and lower surfaces: Smooth, glabrous. Color: When opening, upper and lower surfaces: Close to 145C. Fully opened, upper surface: Close to N57B; color does not change with development. Fully opened, lower surface: Close to N57D; color does not change with development.

*Sepals, fertile flowers*.—Quantity and arrangement: Four in a single whorl. Length: About 2 mm. Width: About 2 mm. Shape: Deltoid. Apex: Retuse. Base: Cuneate. Margin: Entire, undulate. Texture, upper and lower surfaces: Smooth, glabrous. Color: When opening, upper and lower surfaces: Close to 145C. Fully opened, upper and lower surfaces: Close to 145C; color does not change with development.

*Sepals, sterile flowers*.—Quantity and arrangement: Four in a single whorl. Length: About 1.5 cm to 2 cm. Width: About 2 cm. Shape: Deltoid. Apex: Retuse. Base: Cuneate. Margin: Entire, undulate. Texture, upper and lower surfaces: Smooth, glabrous. Color: When opening, upper and lower surfaces: Close to 145C. Fully opened, upper surface: Close to N57C; color does not change with development; when "blued", color becoming closer to 83C. Fully opened, lower surface: Close to N57D; color does not change with development.

*Pedicels, fertile flowers*.—Length: About 5 mm. Diameter: About 2 mm. Strength: Strong. Aspect: About 45° from stem axis. Texture: Smooth, glabrous. Color: Close to N57D.

*Pedicels, sterile flowers*.—Length: About 2 cm. Diameter: About 2 mm. Strength: Strong. Aspect: About 45° from stem axis. Texture: Smooth, glabrous. Color: Close to N57D.

*Reproductive organs, fertile flowers*.—Stamens: Quantity per flower: Eight. Filament length: About 1 mm. Filament color: Close to N57D. Anther length: About 1 mm. Anther shape: Conical. Anther color: Close to N57D. Pollen amount: Abundant. Pollen color: Close to NN155D. Pistils: Pistil quantity per flower: Three. Pistil length: About 3 mm to 4 mm. Stigma shape: Oval. Stigma color: Close to N57D. Style length: About 2 mm to 3 mm. Style color: Close to N57D. Ovary color: Close to N57D.

*Reproductive organs, sterile flowers*.—Stamens: Quantity per flower: About eight. Filament length: About 2 mm. Filament color: Close to 75C. Anther length: About 2 mm. Anther shape: Conical. Anther color: Close to N57D. Pollen amount: Abundant. Pollen color: Close to NN155D. Pistils: Pistil quantity per flower: Three. Pistil length: About 3 mm to 4 mm. Stigma shape: Oval. Stigma color: Close to 150D. Style length: About 2 mm to 3 mm. Style color: Close to 150D. Ovary color: Close to 150D.

*Seeds, only produced by fertile flowers*.—Quantity per fertile flower: About 20 to 30. Length: About 1 mm. Diameter: About 0.2 mm. Color: Close to 200C.

Pathogen & pest resistance: Under commercial production conditions, plants of the new *Hydrangea* have not been observed to be resistant to pathogens and pests common to *Hydrangea* plants to date.

Temperature tolerance: Plants of the new *Hydrangea* have been shown to be tolerant to temperatures ranging from about 3° C. to about 38° C.

It is claimed:

1. A new and distinct *Hydrangea* plant named 'H220914' as illustrated and described.

* * * * *